United States Patent
Schmidt et al.

(10) Patent No.: US 10,872,401 B2
(45) Date of Patent: Dec. 22, 2020

(54) METHOD FOR MERGING AN ANALYSIS DATA RECORD WITH AN IMAGE DATA RECORD, POSITIONING DEVICE, COMPUTER PROGRAM AND ELECTRONICALLY READABLE DATA STORAGE MEDIUM

(71) Applicant: Siemens Healthcare GmbH, Erlangen (DE)

(72) Inventors: Sebastian Schmidt, Weisendorf (DE); Philipp Hoelzer, Baltimore, MD (US)

(73) Assignee: SIEMENS HEALTHCARE GMBH, Erlangen (DE)

( * ) Notice: Subject to any disclaimer, the term of this patent is extended or adjusted under 35 U.S.C. 154(b) by 109 days.

(21) Appl. No.: 16/199,538

(22) Filed: Nov. 26, 2018

(65) Prior Publication Data

US 2019/0172188 A1    Jun. 6, 2019

(30) Foreign Application Priority Data

Dec. 5, 2017   (DE) .................. 10 2017 221 924

(51) Int. Cl.
*G06T 5/00* (2006.01)
*G06T 5/50* (2006.01)
(Continued)

(52) U.S. Cl.
CPC ............. *G06T 5/50* (2013.01); *A61B 6/03* (2013.01); *A61B 6/032* (2013.01); *A61B 6/4417* (2013.01);
(Continued)

(58) Field of Classification Search
None
See application file for complete search history.

(56) References Cited

U.S. PATENT DOCUMENTS

| | | | |
|---|---|---|---|
| 2011/0122993 A1* | 5/2011 | Ichizawa | G21K 1/10 378/51 |
| 2011/0142316 A1* | 6/2011 | Wang | G06T 11/006 382/131 |

(Continued)

OTHER PUBLICATIONS

Hwuang, Eileen et al. "Spectral embedding-based registration (SERg) for multimodal fusion prostate histology and MRI" Proc. SPIE 9034, SPIE Medical Imaging, Image Processing, Mar. 2014 // doi: 10.1117/12.2044317.

(Continued)

*Primary Examiner* — Delomia L Gilliard
(74) *Attorney, Agent, or Firm* — Harness, Dickey & Pierce, P.L.C.

(57) ABSTRACT

A method for merging a three-dimensional analysis data record of a tissue sample of a patient with a three-dimensional image data record of the patient indicating, prior to removal, the removal area of the tissue sample. The method includes registering a three-dimensional intermediate data record of the three-dimensional analysis data record. The registering includes transforming analysis data of the three-dimensional analysis data record into intermediate data, corresponding to image data recorded with a modality with which the three-dimensional image data record has been recorded and including a resolution reduced, to determine the three-dimensional intermediate data record corresponding, in terms of resolution, to the image data record; and registering the three-dimensional intermediate data record with the three-dimensional image data record. Finally, the method includes merging the three-dimensional analysis data record and the three-dimensional image data record using a registration rule obtained during the registering of the three-dimensional intermediate data record.

18 Claims, 2 Drawing Sheets

(51) Int. Cl.
- *A61B 6/00* (2006.01)
- *G06T 19/00* (2011.01)
- *G06T 7/30* (2017.01)
- *A61B 6/03* (2006.01)
- *G16H 30/40* (2018.01)
- *G16H 10/40* (2018.01)
- *G06T 7/33* (2017.01)
- *G06T 3/40* (2006.01)
- *G06T 7/40* (2017.01)
- *A61B 5/055* (2006.01)

(52) U.S. Cl.
CPC .............. *A61B 6/463* (2013.01); *A61B 6/466* (2013.01); *A61B 6/469* (2013.01); *A61B 6/482* (2013.01); *A61B 6/5235* (2013.01); *A61B 6/5247* (2013.01); *A61B 6/5294* (2013.01); *G06T 3/4038* (2013.01); *G06T 7/30* (2017.01); *G06T 7/337* (2017.01); *G06T 7/40* (2013.01); *G06T 19/00* (2013.01); *G16H 10/40* (2018.01); *G16H 30/40* (2018.01); *A61B 5/055* (2013.01); *A61B 6/4241* (2013.01); *A61B 2505/05* (2013.01); *A61B 2576/00* (2013.01); *G06T 2207/10116* (2013.01); *G06T 2207/20081* (2013.01); *G06T 2207/20221* (2013.01); *G06T 2207/30024* (2013.01); *G06T 2210/41* (2013.01)

(56) References Cited

U.S. PATENT DOCUMENTS

| | | | |
|---|---|---|---|
| 2011/0311019 A1* | 12/2011 | Ribbing | G01T 1/2985 378/9 |
| 2013/0053679 A1* | 2/2013 | Owen | A61B 8/4263 600/411 |
| 2014/0050295 A1* | 2/2014 | Dennerlein | A61B 6/52 378/4 |
| 2017/0258411 A1* | 9/2017 | Koehler | A61B 6/405 |
| 2018/0217273 A1* | 8/2018 | Serafino | A61B 6/5282 |
| 2018/0235557 A1* | 8/2018 | Rousso | G01T 1/2985 |
| 2019/0172188 A1* | 6/2019 | Schmidt | G06T 5/50 |

OTHER PUBLICATIONS

German Office Action_Application No. 2017P20980DE / dated Aug. 21, 2018.

* cited by examiner

METHOD FOR MERGING AN ANALYSIS DATA RECORD WITH AN IMAGE DATA RECORD, POSITIONING DEVICE, COMPUTER PROGRAM AND ELECTRONICALLY READABLE DATA STORAGE MEDIUM

PRIORITY STATEMENT

The present application hereby claims priority under 35 U.S.C. § 119 to German patent application number DE 102017221924.6 filed Dec. 5, 2017, the entire contents of which are hereby incorporated herein by reference.

FIELD

At least one embodiment of the invention generally relate to a method for merging a three-dimensional analysis data record of a tissue sample of a patient taken from a patient with a three-dimensional image data record of the patient indicating, prior to removal, the removal area from which the tissue sample has been taken. Embodiments of the invention also relates to a merging device, to a computer program and to an electronically readable data storage medium.

BACKGROUND

It is known to take tissue samples from the body of the patient in order to obtain more accurate information relating to lesions in the human body, for instance tumors. For instance, the tumor or part thereof can be surgically removed during the course of a biopsy. This can be carried out within the scope of a surgical intervention and/or a minimally invasive intervention, using a hollow needle for instance. The tissue sample taken can then be examined more accurately using a microscope, for instance, wherein a plurality of staining methods which enable an accurate assessment of the tissue is available. Tissue samples may be very heterogeneous particularly in the case of tumors. For instance, healthy tissue in addition to adenoma, carcinoma and necrosis can exist in parallel within a tumor.

In fact, imaging methods, for instance computed tomography, magnetic resonance imaging and/or ultrasound imaging, achieve increasingly better resolutions, for instance up to a voxel size of significantly below 1 mm. Increasingly higher resolving x-ray detectors are also being developed as a modality particularly with respect to computed tomography, for instance direct-conversion detectors (also known as photon-counting detectors). However, the resolution still lies by a factor in the range of 100 to 1000 below the resolution of the light microscopy, which can be used when a tissue sample is taken.

It may still be desirable for a radiologist and/or any other physician to be able to perceive the results of the analysis of the tissue sample within the context of the previously surrounding anatomy, in order to draw advanced conclusions, particularly within the scope of the diagnosis, for instance continuing calcifications and suchlike. For instance, the result of the analysis of the tissue sample using light microscopy may be an analysis data record (histological data record), which is to be shown positioned accurately together with an image data record (radiological data record) in order to determine the position in the image data record of the lesion from which the tissue sample originates, which environment is shown and suchlike. To this end, it is only known to use in most cases two-dimensional image recordings which have been recorded when the tissue sample, in particular the biopsy, was taken, in order to realize an image support. Intraoperative image recordings are in most cases of poor quality and thereby provide no diagnostic relevance especially in view of the radiation to be limited with the x-ray imaging and/or the rapid recording desired with other modalities.

It was also proposed to examine tissue samples themselves by way of imaging, for instance x-ray imaging, in order to relocate specific features, for instance calcifications, from a pre-examination, as is described for mammographies, for instance. However, the context relating to an image data record recorded before taking the tissue sample can in most cases also no longer be established meaningfully.

SUMMARY

At least one embodiment of the invention therefore specifies a possibility of accurately registering an analysis data record with an image data record and thus merges the data records.

In at least one embodiment, it is inventively provided in the case of a method that in order to register the analysis data record with the image data record:
for the purpose of determining a three-dimensional intermediate data record which corresponds to the image data record in terms of its resolution, the analysis data of the analysis data record is transformed into intermediate data corresponding to image data recorded with the modality with which the image data record has been recorded and the resolution is reduced accordingly, and
the intermediate data record is registered with the image data record,
wherein the thus obtained registration rule is used to merge the analysis data record and the image data record.

In at least one embodiment, at least one embodiment of the invention also relates to a method for merging a three-dimensional analysis data record of a tissue sample of a patient taken from a patient with a three-dimensional image data record of the patient indicating, prior to removal, a removal area from which the tissue sample has been taken, the method comprising:
registering the three-dimensional analysis data record with the three-dimensional image data record, the registering including
transforming analysis data of the three-dimensional analysis data record into intermediate data, corresponding to image data recorded with a modality with which the three-dimensional image data record has been recorded and including a resolution reduced, to determine a three-dimensional intermediate data record corresponding, in terms of resolution, to the image data record, and
registering the three-dimensional intermediate data record with the three-dimensional image data record; and
merging the three-dimensional analysis data record and the three-dimensional image data record using a registration rule obtained during the registering of the three-dimensional intermediate data record.

In addition to embodiments of the method, at least one embodiment of the invention also relates to a merging device for merging a three-dimensional analysis data record of a tissue sample of a patient taken from a patient using a three-dimensional image data record of the patient indicating, prior to removal, the removal area from which the tissue sample has been taken. At least one embodiment of an inventive merging device has a control device which is configured to carry out a method of at least one embodiment of the inventive type. Here the merging device can be the image recording device for recording the image data record and/or the analysis device for recording the analysis data record and/or form part of at least one of these devices. The control device expediently has an intermediate data record determination unit for determining the intermediate data record from the analysis data record, a registration unit for registering the intermediate data record with the image data record and a merging unit for merging the analysis data record and the image data record on the basis of the determined registration rule. In order to realize further embodiments of the method, further units can naturally be available, for instance a display unit and/or as subunits of the intermediate data record determination unit an assignment unit and/or resolution reduction unit and/or a simulation unit.

A computer program according to at least one embodiment of the invention can be loaded directly into a memory of a control device of a merging device, for instance, and has program segments/modules to perform the steps of a method according to at least one embodiment of the invention when the computer program is executed in the control device of the merging device. The computer program can be stored on an inventive, electronically readable data storage medium, which therefore comprises electronic control information stored thereupon, which comprises at least one described computer program and is embodied such that it carries out at least one embodiment of an inventive method when the data storage medium is used in a control device of a merging device. The data storage medium according to the invention may be in particular a non-transient data storage medium, for instance a CD-ROM.

BRIEF DESCRIPTION OF THE DRAWINGS

Further advantages and details of the present invention result from the example embodiments described below and with the aid of the drawing, in which.

DETAILED DESCRIPTION OF THE EXAMPLE EMBODIMENTS

Figure 1:
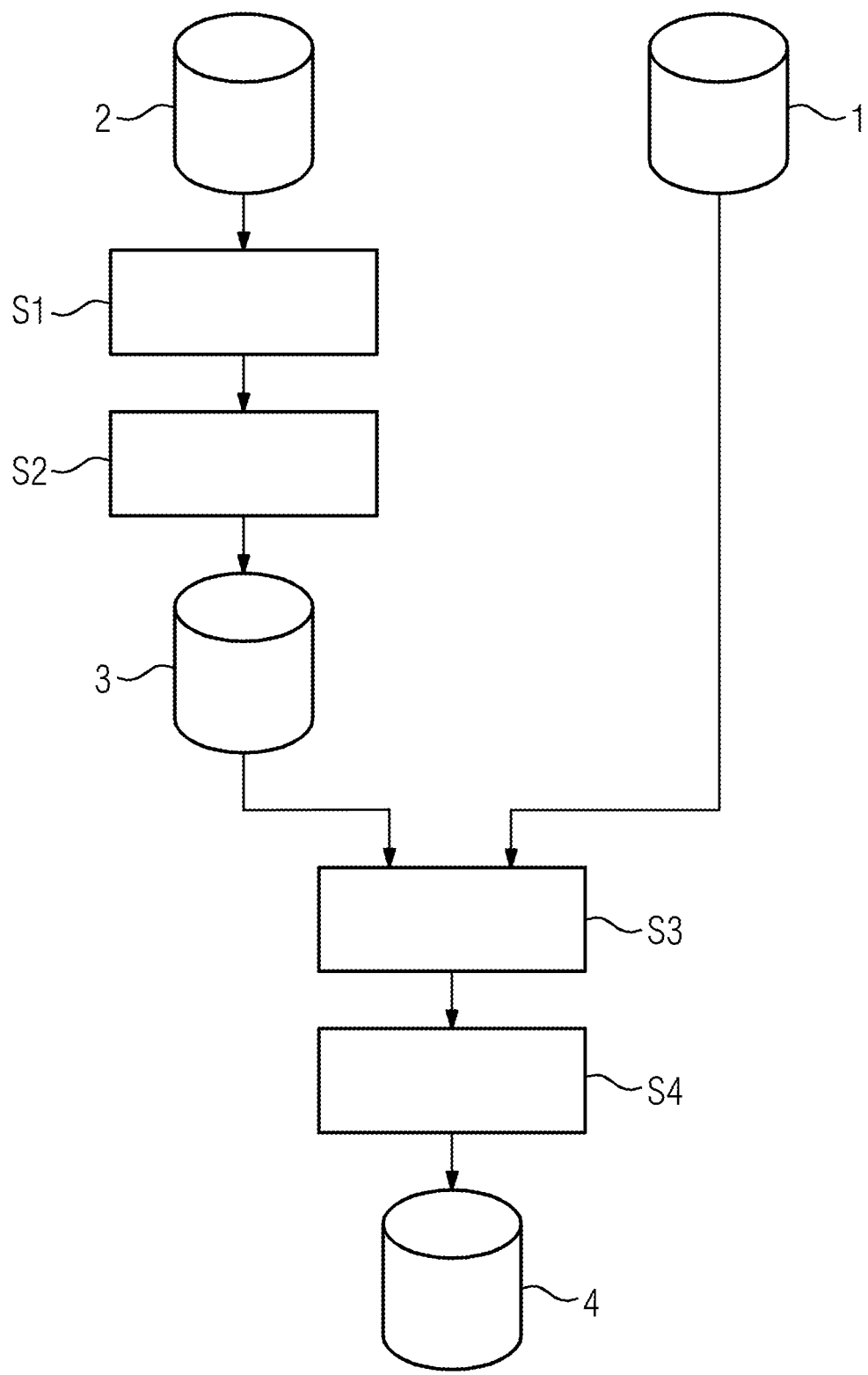
FIG. 1 shows a flow diagram of an example embodiment of the inventive method.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

In at least one embodiment, it is inventively provided in the case of a method that in order to register the analysis data record with the image data record:
for the purpose of determining a three-dimensional intermediate data record which corresponds to the image data record in terms of its resolution, the analysis data of the analysis data record is transformed into intermediate data corresponding to image data recorded with the modality with which the image data record has been recorded and the resolution is reduced accordingly, and
the intermediate data record is registered with the image data record,
wherein the thus obtained registration rule is used to merge the analysis data record and the image data record.

The analysis data record contains the information from the analysis of tissue samples, in particular information from light microscopic recordings, which provide an indication as to the respective tissues in the regions of the tissue sample or describe these explicitly. In accordance with at least one embodiment of the invention, it is now proposed to convert the three-dimensional analysis data record into a pseudo-radiological image, by the resolution being reduced to that of the image data record and it being determined at each voxel which properties this would have in the radiological image. Depending on the procedure, it may be expedient to reduce the resolution before or after a property assignment, therefore combine smaller voxels to form a larger voxel, the size of which corresponds to that of the voxels of the image data record, since the analysis data record is typically recorded in a spatially resolved manner which is significantly higher than the three-dimensional image data record.

Relevant properties or, if possible, directly corresponding image values are therefore assigned to the voxels of the analysis data record for the imaging with the modality of the image data record, so that an intermediate data record is produced, which can be referred to as a pseudo-radiological data record, which with fundamentally known registration methods can be registered with the three-dimensional image data record. In summary, an intermediate data record is therefore generated, which acts like an image recorded with the modality of the image data record, which therefore allows for the immediate, robust and highly accurate use of registration algorithms, such as are known in the prior art. A highly accurate registration and therefore a high-quality merging is allowed in this way, which represents an extremely useful tool within the scope of analyzing/assessing the analysis result of the tissue sample.

In such cases, the method proposed here can be used increasingly better, the more voxels of the resolution of the image data record can be generated from the analysis of the tissue sample, so that an expedient embodiment provides that the tissue sample in at least one expansion direction has at least ten times the size of a voxel of the image data record. In general, the tissue sample should therefore be considerably larger than the minimal spatial resolution of the modality of the image data record, for instance in other words 10×10×10 mm with a local resolution of 0.5 mm. A plurality of voxels of the intermediate data record can be obtained in this way, which supports a reliable and robust registration.

In a specific variant for determining the analysis data record, provision can be made for the tissue sample to be distributed into layers which are examined microscopically. In this way it is also possible to carry out a staining before or after distribution into (physical) layers, in particular in the frozen state, for the purpose of distinguishing between tissue types, wherein a plurality of staining techniques is known. The hematoxylin-eosin stains, often abbreviated to HE stain, and/or the immune marker, in which antibodies are used, are only to be cited by way of example. A microtome can be used to generate layers from the tissue sample, for instance, wherein 10 μm thick layers of the in particular frozen tissue sample can be generated, for instance. These layers can then be examined using a light microscope, so that digital tomographs are produced, which are then merged to form the three-dimensional analysis data record, by the individual digital tomographs being placed one on top of the other. The analysis data record then subsequently contains the information from the light microscopic recordings.

In a specific, preferred embodiment, an intermediate item of data of the intermediate data record and/or an item of tissue data describing a tissue property which relates to the modality of the image data record can be assigned to each voxel of the analysis data record which is in particular already reduced in terms of its resolution, wherein with the use of tissue data, the intermediate data record is determined for comparison with the image data record by simulation of an imaging process of the modality. While it may essentially in many cases be conceivable to deduce an image value directly from the analysis data of the analysis data record, for instance an HU value in the case of computed tomography, this is in practice and in particular also with other modalities of medical imaging not absolutely the case. For instance, the material structure may change as a result of preparing the tissue sample before the analysis.

By washing off the tissue sample, for instance, fat can be replaced by way of vacuoles, which are detected as air, but originally contained no air. Use can be made here of more complex assignment algorithms, in particular those of artificial intelligence, which can structurally identify the vacuoles produced by the washing-off process and carry out a fat assignment. In general terms, an assignment algorithm can therefore carry out an assignment of tissue data and/or image data on account of structure properties in the analysis data record. The use of tissue data and a subsequent simulation of the imaging are expedient particularly with modalities such as ultrasound and magnetic resonance. For instance, impedance jumps are mapped onto acoustic impedance by the ultrasound imaging, said impedance jumps firstly having to be located within the tissue described by the analysis data record.

In particular, in the case of tissue data, depending on the modality, corresponding physical properties, for instance beam density, relaxation times, acoustic impedances and suchlike, are assigned to each voxel. As already mentioned, an assignment algorithm can be used for this purpose. A pseudo-radiological data record, in other words the intermediate data record, is calculated from these physical properties, in other words the tissue data, by the physics of the imaging of the respective modality being simulated, for instance the ultrasound reflection, the magnetic resonance behavior and/or the beam attenuation.

This provides for a particularly preferred embodiment of the invention, wherein during simulation recording parameters which have been used with the recording of the image data record are employed. When the image data record comprises a number of images which have been recorded with different recording parameters, it may then be particularly expedient and for the purpose of expanding the basis for a registration for intermediate images of the intermediate data record for all sets of recording parameters to be determined by way of the simulation. If various recording parameters used when the image data record is recorded are taken into account for the simulation, in order to obtain different intermediate images, more data points exist for the registration, since the respectively associated intermediate images and images of the image data record can be registered with one another. With magnetic resonance imaging, different recording parameters may be different types of magnetic resonance sequences (T1-weighted, T2-weighted, etc.), for instance, with computed tomography different spectral images (dual-energy CT, spectral CT, . . . ) and suchlike. Taking the recording parameters with which the image data record has been recorded into account results overall in a particularly good comparability and therefore possibility of registration.

A further, particularly preferred embodiment in this context provides that the assignment is carried out using an assignment algorithm of artificial intelligence, which has been trained by way of machine learning using registered analysis data records and image data records. The assignment of tissue data (or also image data) is therefore preferably carried out by way of a trainable artificial intelligence assignment algorithm, for instance a neural network, which has previously been trained with the histological and radiological data of tissue samples. Particularly with regard to structural changes during the preparation of the tissue samples, the use of such artificial intelligence assignment algorithms which develop associations themselves has proven useful.

One advantageous development further provides that at least one part of the determination of the intermediate data record and/or the registration is carried out by way of texture analysis. Provision can specifically be made in this context for texture data describing the texture of the in particular already resolution-reduced analysis data record to be determined by texture analysis and to be taken into account when the image data and/or tissue data is assigned and/or for the registration to be carried out by comparing textures of the image data record with the texture of the intermediate data record. Typical metrics within the texture analysis which can be used as texture data comprise the average intensity, the maximum intensity, the minimum intensity, the uniformity, the entropy (regularity of the gray level distribution), the standard deviation of a histogram of the respective data, the "skewness" (asymmetry of the histogram), the kurtosis (flatness of the histogram), the entropy in the sense of the randomness of the matrix, the energy/the second angular moment (voxel repetition/regularity and degree of "co-occurrence matrix"), degree of dissimilarity (degree as to how different each element in the matrix is), degrees of correlation (measurement of linear dependencies in the respective data), degree of the texture in a specific direction ("run-length-matrix"), neighboring gray level difference matrices (spatial relationship between three or more voxels), contrast values (number of local variations within the data record), fineness of grain (degree of the edge density), degree of the spatial rate of the gray level change ("busyness"), heterogeneity (degree of the presence of edges), degree of the non-uniformity ("neighboring gray level dependence matrix") and suchlike. Such texture data allows for an excellent characterization of the texture, in particular with respect to the assignment of image data and/or tissue data, and an excellent comparison of textures, for instance, in order to be able to locate a comparable texture with respect to the texture of the intermediate data record in the image data record.

It should be noted here again that within the scope of at least one embodiment of the present invention, it is also possible to characterize and to consider the inherent noise texture both of the microscope and also of the imaging modality, in particular by removing the respective noise textures in the analysis data record and/or the image data record.

Calibrating the texture of the intermediate data record with the textures of the image data record is preferably carried out in patches. It should be noted here that artificial intelligence registration algorithms can similarly be used expediently in particular to identify the removal position, therefore the location in the image data record to which the tissue sample belongs, wherein within the scope of at least one embodiment of the present invention support vector machines, Bayes classifiers, decision trees, neural networks, deep belief networks and other artificial intelligence and machine learning techniques, for instance deep residual learning, reinforcement learning, k-Means clustering, induc-tive programming and suchlike, can be used overall as artificial intelligence algorithms.

In summary the texture analysis therefore represents a useful expansion in particular with respect to the registration, wherein the texture analysis can preferably be used additionally in the analysis data record which as yet is not resolution-reduced, in order to carry out an assignment, for instance to identify formerly fat-filled vacuoles or suchlike. With the use of texture data in respect of the assignment of image data and/or tissue date, the original three-dimensional analysis data record is therefore preferably geared to the original voxels, which are combined to form a larger voxel, with respect to the assignment of image data and/or tissue data.

It should be noted again at this point that with the resolution reduction fundamentally known possibilities can be used, for instance average value formations, other statistical analyses and/or the assignment of the tissue type occurring at most to the large voxel.

In a preferred embodiment, for registration purposes a rough positioning of the analysis data record with respect to the image data record can firstly take place by using intraoperative auxiliary images recorded with the removal of the tissue sample and registered with the image data record, wherein the rough position is used as a starting point for the registration. Intraoperative auxiliary images, for instance two-dimensional fluoroscopy images, which are registered with the image data record, can therefore be used particularly advantageously, in order firstly to roughly localize the removal region, after which the fine registration of the intermediate data record with the image data record is carried out. The reliability and robustness of the registration is increased further here.

It is further advantageous if a direct-conversion detector and/or a recording protocol allowing for a higher resolution in an area containing the tissue sample on account of a higher radiation dose is used as an x-ray detector to record the image data record during the x-ray imaging, in particular computed tomography. The use of a direct-conversion detector, in other words a photon-counting detector, is particularly advantageous in computed tomography. This is particularly favorable because on the one hand the resolution from which the registration profits is higher, on the other hand however a spectral separation is available, which allows the boundaries of different tissue types to be better contrasted. In this regard, a recording protocol can be used expediently, which uses a higher radiation dose locally in the region of the lesion/tissue sample, in order to allow for a higher resolution; with the reduction in the resolution of the analysis data record, in this regard the resolution of the image data record in the removal region is naturally to be processed with different resolutions across the image data record.

In one development of at least one embodiment of the present invention, provision can be made for the merging to be carried out by way of superimposition and/or with a representation of the merging data record obtained as a result of the merging for a zoom function to be provided and/or prior to the merging for a reformatting of the analysis data record to be carried out in order to adjust to a type of visualization, in particular a sectional plane, of the image data record. Expediently the merging data record is shown subsequently or at a later point in time, wherein a superimposition of histological analysis data with the radiological image data is particularly expedient, so that both are shown jointly to the observer, in particular an assessor. A zoom function is expedient, in order to be able to zoom into the display. Since the histological image is present as a three-dimensional analysis data record, it can be reformatted, for instance within the scope of a multiplanar reformation, in order to adjust the viewing position to the displayed image of the image data record.

In addition to the method, at least one embodiment of the invention also relates to a merging device for merging a three-dimensional analysis data record of a tissue sample of a patient taken from a patient using a three-dimensional image data record of the patient indicating, prior to removal, the removal area from which the tissue sample has been taken. At least one embodiment of an inventive merging device has a control device which is configured to carry out a method of at least one embodiment of the inventive type. Here the merging device can be the image recording device for recording the image data record and/or the analysis device for recording the analysis data record and/or form part of at least one of these devices. The control device expediently has an intermediate data record determination unit for determining the intermediate data record from the analysis data record, a registration unit for registering the intermediate data record with the image data record and a merging unit for merging the analysis data record and the image data record on the basis of the determined registration rule. In order to realize further embodiments of the method, further units can naturally be available, for instance a display unit and/or as subunits of the intermediate data record determination unit an assignment unit and/or resolution reduction unit and/or a simulation unit.

A computer program according to at least one embodiment of the invention can be loaded directly into a memory of a control device of a merging device, for instance, and has program segments/modules to perform the steps of a method according to at least one embodiment of the invention when the computer program is executed in the control device of the merging device. The computer program can be stored on an inventive, electronically readable data storage medium, which therefore comprises electronic control information stored thereupon, which comprises at least one described computer program and is embodied such that it carries out at least one embodiment of an inventive method when the data storage medium is used in a control device of a merging device. The data storage medium according to the invention may be in particular a non-transient data storage medium, for instance a CD-ROM.

FIG. 1 shows a flow diagram of an example embodiment of the inventive method, with which an image data record 1, which is a computed tomography data record (CT data record) here and has been recorded with a computed tomography device as an image recording device, and an analysis data record 2 of a tissue sample of the patient, which has been taken after the image data record 1 has been recorded, are to be merged. The image data record 1 has been recorded here using a direct-conversion detector as an x-ray detector and a recording protocol which allows for a higher radiation intensity in the region of the lesion to which the tissue sample belongs. The image data record 1 is therefore high-resolution at least in the removal area from which the tissue sample was subsequently taken, wherein the resolution is still significantly lower than that of the analysis data record 2 which has been determined for instance by dividing the tissue sample using a microtome, applying histological staining methods and light microscopy using a microscope. The tissue sample is still considerably larger than the extent of the voxels of the image data record 1, which define the best possible local resolution. The analysis data record 2 may have been determined for instance using an analysis device, with which the division into different layers, the staining method and the light microscopy can be implemented, so that the three-dimensional analysis data record 2 is determined by overlaying the information from the microscopy of the layers.

Within the scope of the merging method described here, an intermediate data record 3 is now firstly to be determined from the analysis data record 2, the intermediate data of which corresponds to image data recorded with the modality of the image data record 1, here in other words the computed tomography. To this end, in a step S1, a resolution reduction of the analysis data record 2 to the resolution in the removal area of the image data record 1 is firstly carried out, wherein tissue data which in a step S2 allows the intermediate data record 3 to be determined by simulating the imaging process of the computed tomography is assigned in each case to the thus produced larger voxels in each case. The tissue data is assigned here using an artificial intelligence assignment algorithm, which, from the analysis data of a larger voxel composed of a number of smaller voxels of the analysis data record 2, assigns corresponding tissue data relevant to the modality of the image data record 1. In particular, texture data of a texture analysis which has been performed prior to the resolution reduction can also be taken into account here; in each case it is expedient if a structure analysis of any type is carried out by the assignment algorithm, since changes occurring for instance by preparing the tissue sample, for instance replacing fat with air-filled vacuoles, can be identified and handled correctly. The structure analysis can also take place in a different way to a texture analysis, wherein the latter is preferably used, however.

With the resolution reduction, known statistical procedures are fundamentally applied, in a simple embodiment, for instance, an average value formation relating to contained tissue classes or the assignment of the most frequently occurring tissue class and the corresponding tissue data.

There is therefore information in step S2 which is required in order to simulate the imaging, which in the case of computed tomography imaging with a known tissue type in a voxel can be carried out relatively directly, since HU values, therefore image data, can be assigned directly to tissue types which can be described by the tissue data, for instance; virtual projections and suchlike are naturally also usable, however. The method described here can naturally also be applied to image data records 1 of other modalities, in particular the magnetic resonance and/or the ultrasound imaging, wherein more complex simulations in step S2 can occur here.

In a step S3, the intermediate data record 3 is then registered with the image data record 1, wherein this is currently carried out in two steps. The presence of auxiliary images which have been recorded for image support of the removal of the tissue sample, is firstly used, since in these auxiliary images, which are also registered with the image data record 1, it is roughly apparent where the tissue sample has been taken, so that a first rough positioning is carried out in a first substep of the step S3. On the basis of this rough positioning, the fine registration is then carried out with fundamentally known registration algorithms.

It should be noted again at this point that the recording parameters which have been used to record the at least one image of the image data record 1 have also been taken into account in step S2 with the simulation of the imaging in order to obtain the intermediate data record 3, so that an excellent comparability of the intermediate data record 3 and the image data record 1 exists, which simplifies registration. A corresponding intermediate image of the intermediate data record 3 is also available for each image of the image data record 1, which has been recorded with different recording parameters.

A specific variant of the registration in step S3 can likewise be realized by texture analysis. In this regard the texture of the intermediate data record 3 is described by texture data, wherein the corresponding texture of the intermediate data record 3 is compared in patches with textures of the image data record 1, in order to define a match. An artificial intelligence registration algorithm can also be used here, for instance a neural network.

The result of step S3 is a registration rule, which is used in step S4 to merge the analysis data record 2 and the image data record 1 in order to form a merging data record 4. A superimposition preferably takes place here, so that an observer can observe the histological information and the radiological information at the same time.

Figure 2:
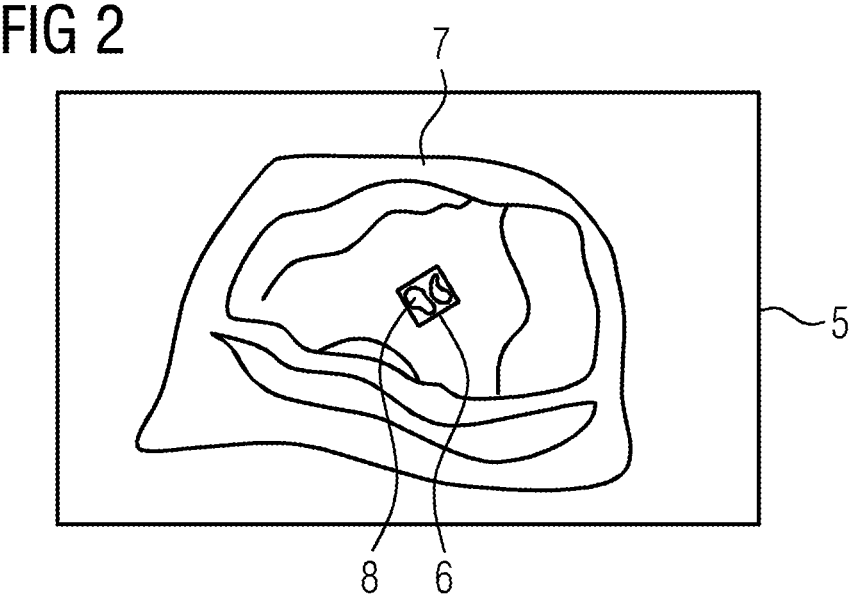
FIG. 2 shows a possible display of a merging data record.

One possible display 5 is shown schematically in FIG. 2. The histological information 8 of the analysis data record 2 is inserted into the radiological information 7 of the image data record 1 at the removal point 6, which has been located by way of the registration in step S3. A provided zoom function allows the removal point 6 and the information 7, 8 superimposed there to be observed more clearly. Since the analysis data record 2 is three-dimensional, a display adjusted to the corresponding layers of the three-dimensional image data record 1 can be generated by corresponding reformation techniques, for instance by multiplanar reformation (MPR).

Figure 3:
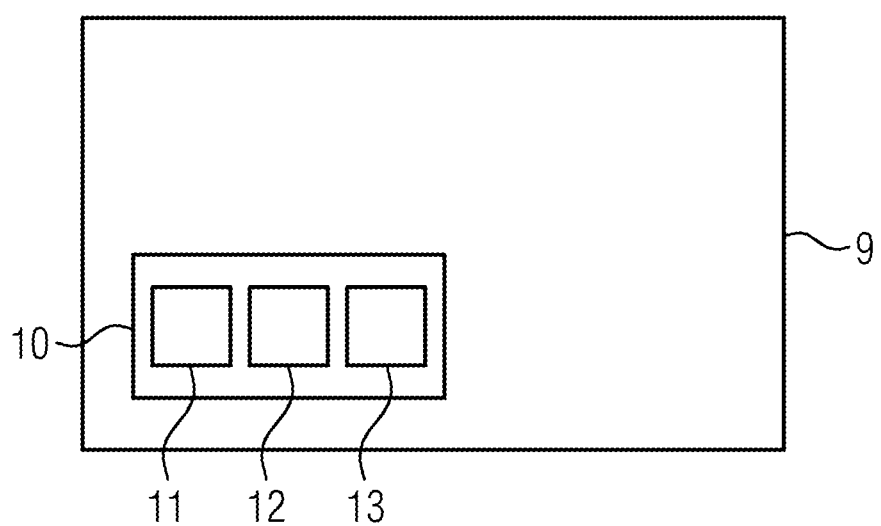
FIG. 3 shows an example embodiment of an inventive merging device.

FIG. 3 finally shows a schematic diagram of an inventive merging device 9, which comprises a control device 10 embodied to carry out the inventive method. To this end, the control device 10 can inter alia have an intermediate data record determining unit 11, a registration unit 12 and a merging unit 13 for carrying out the respective steps. The merging device 9 can be realized as part of an image recording device and/or an analysis device.

Although the invention has been illustrated and described in detail with the preferred example embodiment, the invention is not restricted by the examples given and other variations can be derived therefrom by a person skilled in the art without departing from the protective scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for merging a three-dimensional analysis data record of a tissue sample of a patient taken from a patient with a three-dimensional image data record of the patient indicating, prior to removal, a removal area from which the tissue sample has been taken, the method comprising:
   registering a three-dimensional intermediate data record of the three-dimensional analysis data record, with the three-dimensional image data record, the registering including
      transforming analysis data of the three-dimensional analysis data record into intermediate data, the intermediate date corresponding to image data recorded with a modality with which the three-dimensional image data record has been recorded, and having a reduced resolution, such that the three-dimensional intermediate data record corresponds, in terms of resolution, to the image data record,
      assigning at least one of an intermediate item of data of the three-dimensional intermediate data record and an item of tissue data describing a tissue property which relates to the modality of the three-dimensional image data record, to each voxel of the three-dimensional analysis data record, wherein the three-dimensional intermediate data record is determined by simulation of an imaging process of the modality using the item of tissue data; and
   merging the three-dimensional analysis data record and the three-dimensional image data record using a registration rule obtained during the registering of the three-dimensional intermediate data record.

2. The method of claim 1, wherein the tissue sample, in at least one expansion direction, is at least ten times a size of a voxel of the three-dimensional image data record.

3. The method of claim 1, wherein, to determine the three-dimensional analysis data record, the tissue sample is divided into layers, and examined microscopically.

4. The method of claim ,1 wherein recording parameters of the three-dimensional image data record are used with the simulation of the imaging process.

5. The method of claim 4, wherein the three-dimensional image data record includes a number of images, having been recorded with different recording parameters, and wherein the three-dimensional image data record, including the number of images, is used in determining intermediate images of the three-dimensional intermediate data record for all sets of recording parameters.

6. The method of claim 1, wherein the assigning is carried out using an artificial intelligence assignment algorithm, trained by machine learning by way of registered three-dimensional analysis data records and three-dimensional image data records.

7. The method of claim 1, wherein at least one part of at least one of the transforming to determine the three-dimensional intermediate data record and the registering is carried out by texture analysis.

8. The method of claim 7, wherein at least one of texture data, describing a texture of the three-dimensional analysis data record, is determined by the texture analysis and is taken into account when assigning at least one of image data and the item of tissue data and the registering is carried out by comparing textures of the three-dimensional image data record with a texture of the three-dimensional intermediate data record.

9. The method of claim 1, wherein, for registration purposes, a rough positioning of the three-dimensional analysis data record with respect to the three-dimensional image data record is firstly performed using intraoperative auxiliary images recorded with the removal of the tissue sample, registered with the three-dimensional image data record, and wherein the rough positioning is used as a starting point for the registering.

10. The method of claim 1, wherein at least one of a direct-conversion detector and a recording protocol, allowing for a higher resolution in an area containing the tissue sample on account of a higher radiation dose, is used as an x-ray detector to record the three-dimensional image data record during x-ray imaging.

11. The method of claim 1, wherein at least one of
the merging is carried out by way of superimposition,
a zoom function is provided with a display of a three-dimensional merging data record obtained as a result of the merging, and
prior to the merging, a reformatting of the three-dimensional analysis data record is carried out to adjust to a type of visualization of the three-dimensional image data record.

12. A merging device, comprising:
a control device, embodied to
register a three-dimensional intermediate data record of a three-dimensional analysis data record, with a three-dimensional image data record, the control device being embodied, to register three-dimensional intermediate data record, to transform analysis data of the three-dimensional analysis data record into intermediate data, the intermediate data corresponding to image data recorded with a modality with which the three-dimensional image data record has been recorded and having a reduced resolution, such that the three-dimensional intermediate data record corresponds, in terms of resolution, to the image data record, assign at least one of an intermediate item of data of the three-dimensional intermediate data record and an item of tissue data describing a tissue property which relates to the modality of the three-dimensional analysis data record, wherein the three-dimensional intermediate data record is determined by simulation of an imaging process of the modality using the item of tissue data; and merge the three-dimensional analysis data record and the three-dimensional image data record using a registration rule obtained during the registering of the three-dimensional intermediate data record.

13. A non-transitory computer readable medium storing a computer program, the computer program including program segments that, when executed on a control device of a merging device, perform the method of claim 1.

14. A non-transitory electronically readable data storage medium, storing a computer program to, when executed on a control device of a merging device, perform the method of claim 1.

15. The method of claim 2, wherein, to determine the three-dimensional analysis data record, the tissue sample is divided into layers, examined microscopically.

16. The method of claim 1, wherein the three-dimensional analysis data record is already reduced in terms of resolution.

17. The method of claim 1, wherein the tissue data includes at least one of instance beam density, relaxation times, and acoustic impedances, based on the modality.

18. The merging device of claim 12, wherein the tissue data includes at least one of instance beam density, relaxation times, and acoustic impedances, based on the modality.

* * * * *